United States Patent [19]

Tuba et al.

[11] Patent Number: 5,410,040
[45] Date of Patent: * Apr. 25, 1995

[54] DIAMINO-ANDROSTANE DERIVATIVES

[75] Inventors: Zoltan Tuba; Judit Horváth; Maria Lovas nee Marsai, all of Budapest, Hungary; Miklos Riesz, deceased, late of Budapest, Hungary, by Maria Reisz nee Kateu, legal representative; Katalin Biró, Budapest, Hungary; Lászlé Szporny, Budapest, Hungary; Egon Kárpati, Budapest, Hungary

[73] Assignee: Richter Gedeon Vegyeszeti Gyar Rt., Budapest, Hungary

[ * ] Notice: The portion of the term of this patent subsequent to Jul. 25, 2008 has been disclaimed.

[21] Appl. No.: 879,805

[22] Filed: Jun. 27, 1986

[30] Foreign Application Priority Data

Jul. 1, 1985 [HU] Hungary .............................. 2553/85

[51] Int. Cl.$^6$ ........................ A61K 31/58; C07J 43/00
[52] U.S. Cl. ...................................... 540/96; 514/176
[58] Field of Search ........................................... 540/96

[56] References Cited

U.S. PATENT DOCUMENTS

| | | | |
|---|---|---|---|
| 3,553,212 | 1/1971 | Hewett et al. | 260/239.5 |
| 4,071,515 | 1/1978 | Tuba et al. | 260/239.5 |
| 4,177,190 | 12/1979 | Tuba et al. | 260/239.5 |

FOREIGN PATENT DOCUMENTS

| | | |
|---|---|---|
| 359218 | 10/1980 | Austria . |
| 0208497 | 1/1987 | European Pat. Off. . |
| 2526788 | 12/1976 | Germany . |
| 2634337 | 11/1978 | Germany . |
| 1042292 | 9/1966 | United Kingdom . |
| 1398050 | 6/1975 | United Kingdom . |

OTHER PUBLICATIONS

Proceedings Of The Int'ntl Symposium On Instrumental High Performanc Thin-Layer Chromatography, 2nd, 1982 pp. 186–194, E. Janos et al.
Chem-Biol Interactions, 6, pp. 351–365 (1973).

Primary Examiner—Nicholas Rizzo
Attorney, Agent, or Firm—Herbert Dubno; Jonathan Myers

[57] ABSTRACT

New monoquaternary and diquaternary 5-alpha-hydroxy-3,16-diaminoandrostane salts are disclosed with curare-like muscle relaxant activity. The new salts are characterized by a surprisingly rapid onset time.

10 Claims, No Drawings

DIAMINO-ANDROSTANE DERIVATIVES

The invention relates to new diamino-androstane derivatives, to a process for their preparation and pharmaceutical compositions containing them as active ingredient. More particularly, the invention concerns new 6,16-diamino-androstane derivatives of the formula (I).

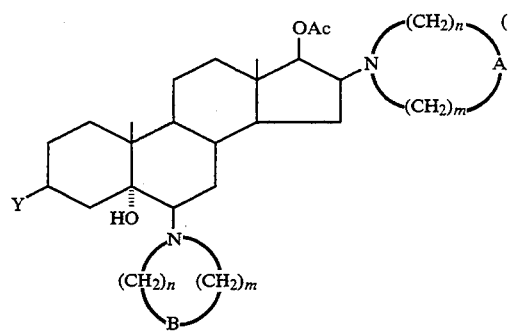

and physiologically acceptable diquaternary and monoquaternary salts thereof having the formula (Ia)-(Id):

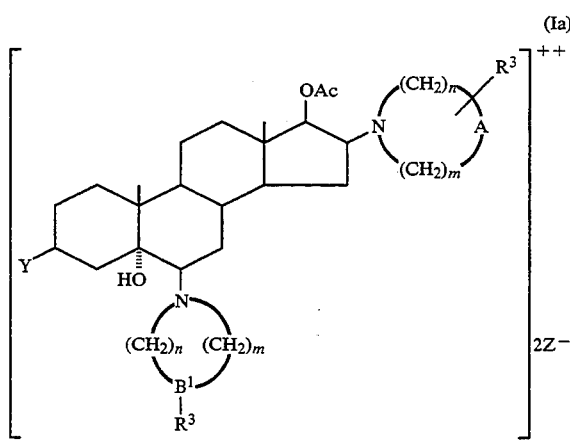

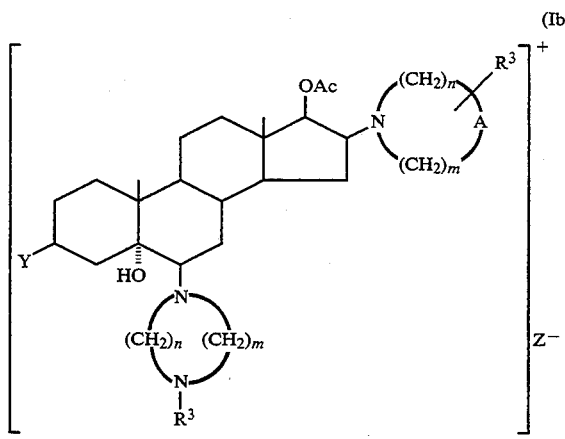

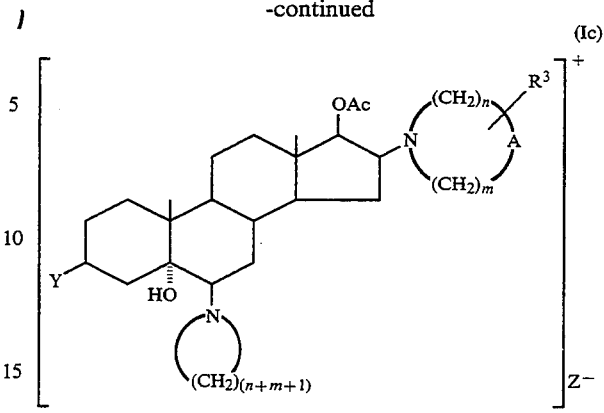

and

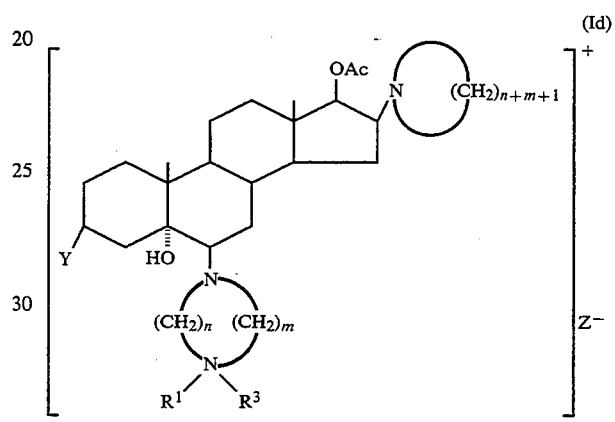

In the formula (I)
  Y is hydrogen or an —OAc group,
  Ac is an alkylcarbonyl group having from 1 to 4 carbon atoms in the alkyl moiety,
  A is methylene or a group of the formula $>N-R^1$, in which $R^1$ is alkyl having from 1 to 4 carbon atoms,
  B is methylene, or a group $>N-R^1$ or $>N-R^2$, in which $R^1$ is as defined above and $R^2$ is a —CH$_2$—CH$_2$—COOR$^1$ group, and
  n is 1 or 2,
  m is 1, 2 or 3.
In the formula (Ia)
  $B^1$ is a group $>N-R^1$ or $>N-R^2$, in which $R^1$ and $R^2$ are as defined above,
  $R^3$ is alkyl or alkenyl having from 1 to 4 carbon atoms,
  Z is halogen or sulfonyloxy, and
  Y, Ac, A, n and m have the same meanings as defined above.
In the formulae (Ib), (Ic) and (Id) the substituents are as defined in connection with the formulae (I) and (Ia), respectively.

There are certain 2,16-diamino-androstane derivatives known in the art, which show curare-like muscle relaxant activity. Of these the compounds disclosed in the U.S. Pat. No. 3,553,212 have a shortened duration of activity, while compounds with a more extended action are disclosed in the British Patent Specification No. 1,398,050. Since the administration of these compounds is far from being free from any risk, extensive research is going on to find new derivatives with an extremely short or intermediate duration of activity or having an onset time as close to administration as possible.

Our research activity in this field resulted in the biologically active 6,16-diamino-androstane derivatives of the formula (I) and their diquaternary or monoquaternary salts encompassed by the formulae (Ia), (Ib), (Ic) and (Id), respectively.

The activity data are set forth in the following Table in comparison with pancuronium bromide, the best compound disclosed in the U.S. Pat. No. 3,553,212, which exerts its activity according to a non-depolarizing mechanism [Negwer (1971) 4821].

| No. of the Example disclosing the test compound | onset time (sec.) |
| --- | --- |
| 46 | 41 |
| 47 | 21 |
| 48 | 20 |
| 53 | 30 |
| 57 | 22 |
| 58 | 27 |
| 61 | 17 |
| pancuronium bromide | 55 |

To determine the time when they begin to exert their activity, the compounds according to the invention were administered in equiactive doses resulting in extremital paralysis in 90 to 100% of the test animals. The tests were carried out on male albino mice, following the method of Pradhan and De [Br. J. Pharmacol. Chemoter. 8:399–405 (1953)], testing each compound in 4 to 6 different doses on 10 animals each time. The compounds were administered intravenously and the period between the injection and myoparalysis was defined as onset time. The results show that the effect of the new compounds (at the same extent of muscle relaxation) developed within a substantially shorter time after administration than that of pancuronium bromide.

It is known that the non-depolarizing muscle relaxants with a more clear activity profile are preferred in therapy to the compounds acting according to a depolarizing mechanism. The reason why the depolarizing muscle relaxants are still widely employed in surgery as initiators of surgical muscle relaxation (intubation) and at short intervals is that their action develops rapidly after the administration of doses resulting in the desired degree of muscle relaxation. In the case of the hitherto known non-depolarizing muscle relaxants the same quick action can be achieved only by relative overdosage, which extends the duration of activity and exposes the patient to an unnecessary drug load. The compounds according to the invention have a satisfactorily short start of action even in the minimum therapeutical doses, have a non-depolarizing action mechanism, i.e. inhibit the transmittance of the nervous stimulus on the striated muscle without initial depolarization and muscle twitching. Their effect can be antagonized with acetyl cholinesterase inhibitors, e.g. neostigmine. They have no influence on the blood circulation and have no hormonal effect.

The new compounds were synthesized starting from the compounds of the formula (VIII)

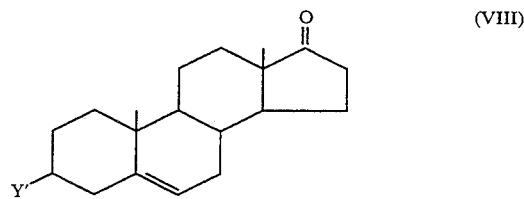

or

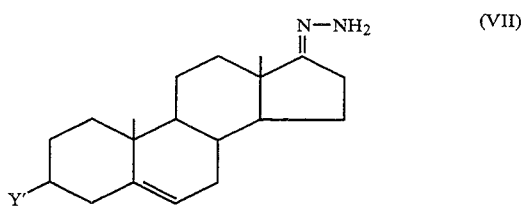

wherein Y' is hydrogen or hydroxyl. Certain representatives of the compounds of the formulae (VIII) and (VII) are known in the art [D. H. R. Barton: J. Chem. Soc. 1962, 470–476 and Tetrahedron Letters 24, 1605–1608 (1983); M. Numazava: Steroids, 32, 519–527 (1978)] while others are new. Preparation of the new compounds is illustrated by Example 2.

From the compounds of formula (VIII) new compounds encompassed by the formula (VI)

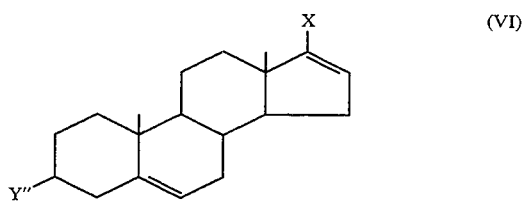

wherein
Y" is hydrogen, hydroxyl or an —OAc group, in which Ac is as defined above,
X is bromine or an —OAc group,
were prepared by two different reaction routes.

The compounds of formula (VI), in which both Y" and X represents an —OAc group were prepared by reacting a compound of the formula (VIII) with the anhydride of an alkanecarboxylic acid having from 1 to 4 carbon atoms or with an alkenyl acetate containing from 2 to 5 carbon atoms in the alkenyl moiety, in the presence of an acid, such as sulfuric acid, p-toluene-sulfonic acid, etc.

The compounds of the formula (IV), in which Y" represents hydrogen or hydroxyl and X is bromine were prepared by converting a compound of the formula (VIII) into a compound of the formula (VII) by reaction with hydrazine hydrate in the presence of a tertiary amine (Y' is as defined above) and transforming the latter compound with N-bromo-succinimide into a compound of the formula (VI) (Y" is hydrogen or hydroxyl, X is bromine) at a temperature between 0° C. and 10° C., in the presence of pyridine.

The compounds of the formula (VI) were then converted into the new diepoxyandrostanes of the formula (V)

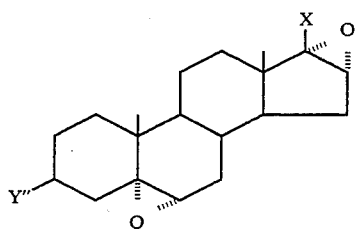

wherein Y'' and X are as defined above, by reaction with a peracid (preferably perbenzoic acid, m-chloroperbenzoic acid, peracetic acid) in an inert organic solvent, such as benzene, chlorinated hydrocarbons, ethers, etc.

The diepoxyandrostanes of the formula (V) are then reacted with an amine of the formula (IX)

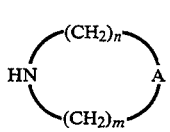

wherein A, n and m are as defined above. Depending on the reaction conditions either the new 16-amino-androstanes of the formula (IV)

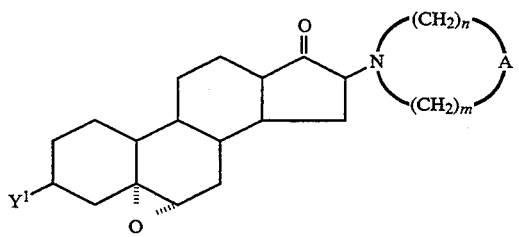

or the new 6,16-diamino-androstanes

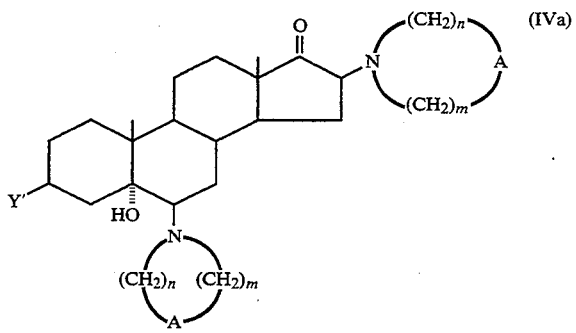

are obtained. In the formulae (IV) and (IVa) the substituents are as defined above. If a compound of the formula (V) is reacted with an amine of the formula (IX) in the presence of an inert organic solvent, e.g. acetonitrile at room temperature or under boiling for a short time (about 2 hours), a 16-monoamino-product of the formula (IV) is obtained. If the reaction is performed under heating over a longer period (about 100 hours) in the presence of water, a 6,16-diamino-product of the formula (IVa) is obtained.

The compounds of the formula (IV) may be converted into the corresponding new compounds of the formula (II)

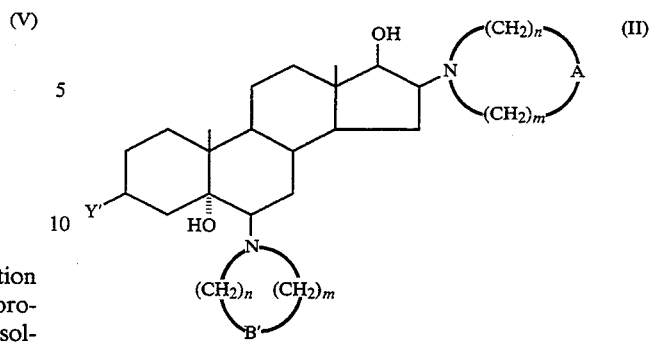

through the compounds of the formula (III)

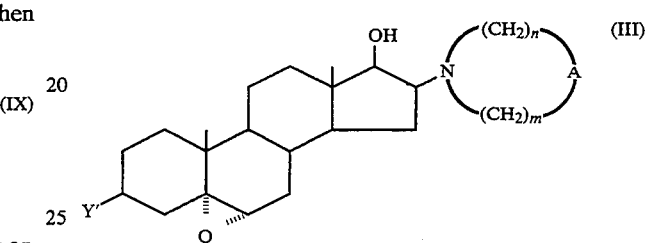

while from the compounds of the formula (IVa) compounds of the formula (II), which are the starting compounds in the process according to the invention, may be directly obtained. In the formula (II)

B' is methylene, a group $>NR^1$ or $>NH$, in which $R^1$ is as defined above,

Y', A, n and m are defined above.

The compounds of the formula (IV) are reduced into the compounds of the formula (III) with a boron complex, preferably sodium, calcium or trimethoxy borohydride, in an alcoholic medium, and the desired new compounds of the formula (II) are obtained by reacting the compound of the formula (III) obtained with an amine of the formula (X)

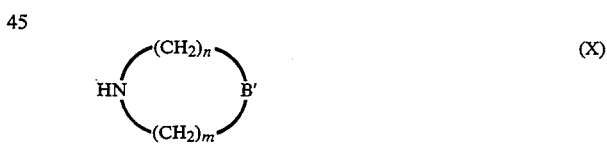

The amine of the formula (X) is reacted with the compound of the formula (III) in the presence of water, at elevated temperature (about 100° C.). In the formulae (III) and (X) the substituents have the same meanings as defined hereinabove.

By reducing the compounds of the formula (IVa) with a complex metal hydride compound of the formula (II), in which B'=A and the other substituents are as defined above, are obtained. As a complex metal hydride the borohydrides mentioned above may be employed in alcohol but lithium aluminium hydride is equally suitable in an ether-type solvent.

The compounds of formula (II), in which B' is an $>N—R^1$ group, if desired, may be converted into the diquaternary salts of the formula (IIa)

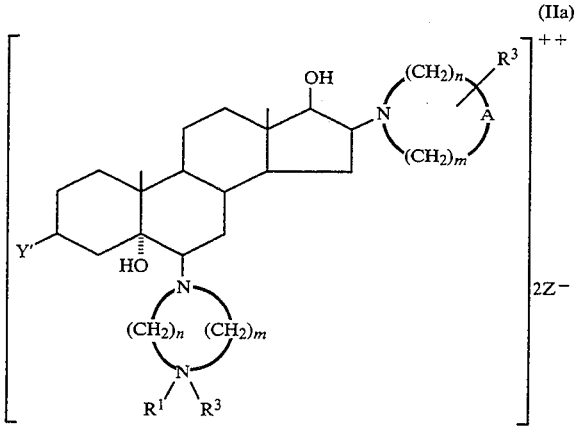

(IIa)

Similarly, from the compounds of the formula (II), in which B' is methylene the monoquaternary salts of the formula (IIb)

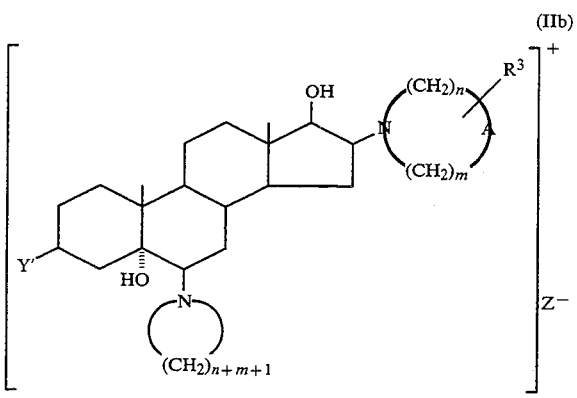

(IIb)

may be prepared, Quaternization is carried out by methods known per se, e.g. by using a reactant of the formula (XI)

$R^3-Z$  (XI)

In the formulae (IIa), (IIb) and (XI) the substituents are as defined above.

The compounds of the formula (I) are prepared by acylating compounds of the formula (II). Alternatively the compounds of the formula (II), in which B' represents an >NH group first are converted into compounds of the formula (IIc)

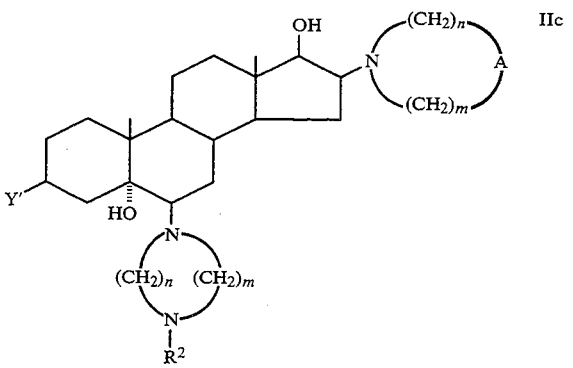

IIc wherein A, Y', $R^2$, n and m are as defined above, and then the compounds of the formula (IIc) are acylated yielding the compounds of formula (I).

The compounds of the formula (I) may be converted into their diquaternary salts of the formula (Ia) or monoquaternary salts of the formulae (Ic) or (Id) by known techniques. The monoquaternary salts of the formula (Ib) may be prepared from the diquaternary salts of the formula (Ia) in an original manner, by adjusting the pH of the reaction mixture to 8.5 to 9. The formation of the desired monoquaternary salts takes place at lower pH as well, but slower.

According to an aspect of the invention there is provided a process for the preparation of the new 6,16-diamino-androstane derivatives of the formula (I) and physiologically acceptable di- and monoquaternary salts thereof, having the formulae (Ia) and (Ib), (Ic and (Id), respectively.

In the formula (I)
Y is hydrogen or an —OAc group,
Ac is alkylcarbonyl having from 1 to 4 carbon atoms in the alkyl moiety,
A is methylene or a group >N—$R^1$, in which $R^1$ is alkyl having from 1 to 4 carbon atoms,
B is methylene, or a group >N—$R^1$ or >N—$R^2$, in which $R^1$ is as defined above, $R^2$ is a substituent of the formula —$CH_2$—$CH_2$—$COOR^1$,
and
n is 1 or 2,
m is 1, 2 or 3, and in the formula (Ia)
$B^1$ is a group >N—$R^1$ or >N—$R^2$, in which $R^1$ and $R^2$ are as defined above,
$R^3$ is alkyl having from 1 to 4 carbon atoms or is allyl,
Z is halogen or sulfonyloxy, and
Ac, Y, A, n and m are as defined above, and in the formulae (Ib), (Ic) and (Id) the substituents are as defined above.

The compounds of the formula (I) and their mono- and diquaternary salts are prepared $a_1$) by reacting a compound of the formula (II), in which
Y' is hydrogen or hydroxyl,
B' is methylene, an >N—$R^1$ or an >NH group, and
A, n and m are as defined above, with an alkanecarboxylic acid derivative containing from 1 to 4 carbon atoms in the alkyl moiety, capable of acylation, or by first reacting a compound of the formula (II), in which B' is an >NH group with a $C_{1-4}$-alkyl ester of acrylic acid, and reacting the compound of the formula (IIc) obtained, in which A, Y', $R^2$, n and m are as defined above, with the above alkanecarboxylic acid derivative capable of acylation, and converting the compound of the formula (I) obtained with a quaternizing agent of the formula (XI), in which $R^3$ and Z are as defined above, into a diquaternary salt of the formula (Ia), or converting a compound of the formula (I) obtained, in which A and B are methylene, into the monoquaternary salts of the formulae (Id) and (Ic), respectively, and if desired, converting a diquaternary salt of the formula (Ia), in which $B^1$ stands for an >N—$R^2$ group into a corresponding monoquaternary salt of the formula (Ib), by adjusting the pH of the reaction mixture to 8.5 to 9, or $a_2$) reacting a compound of the formula (I) with a quaternizing agent of the formula (XI), in which $R^3$ and Z are as defined above, to yield the corresponding diquaternary salt of the formula (Ia) or converting a compound of the formula (I), in which A and B are methylene, into a monoquaternary salt of the formula (Id) or (Ic), and if desired, converting the diquaternary salt of the formula (Ia), in which $B^1$ is a group $>NR^2$, into a monoquaternary salt of the formula (Ib), by adjusting the pH of the reaction mixture to 8.5 to 9.

In the process according to the invention new compounds of the formula (II) are used as starting materials. The compounds of formula (II), in which B' represents an >NH group are first converted into the new compounds of the formula (IIc) by means of a $C_{1-4}$-alkyl ester of acrylic acid. The reaction is preferably carried out at room temperature, in the presence of an inert organic solvent. As a medium generally halogenated hydrocarbons, preferably chloroform are employed. When the reaction is complete, the solvent and the excess of acrylic ester are distilled off, and if desired, the compound of the formula (IIc) obtained is further purified by crystallization.

The compounds of the formula (IIc) and (II), respectively are then converted into the corresponding compounds of the formula (I) by acylation.

The acylation is carried out with an alkanecarboxylic acid derivative capable of acylation. As a derivative capable of acylation generally acid halides or anhydrides are employed, in the presence of an inert organic solvent, preferably chlorinated hydrocarbon (e.g. dichloromethane) or an ether-type solvent (e.g. dioxane). In certain cases the reaction is accomplished in the presence of a tertiary amine, preferably triethyl amine, which serves both as an acid binding agent and a catalyst in the same time, or in the presence of a catalyst, preferably 4-dimethyl-amino-pyridine, alone.

The acylation is preferably carried out at room temperature. When the reaction is complete, the excess of the acylating agent is decomposed and the product is isolated by extraction following evaporation and optionally crystallization. When the acylation is carried out with acetic anhydride, the reaction may be performed also in glacial acetic acid, in the presence of an Lewis acid, e.g. zinc chloride.

The compounds of the formula (I) are then converted into the diquaternary salts of the formula (Ia) or the monoquaternary salts of the formula (Ic) or (Id). In the quaternary salts, if A stands for an $>N-R^1$ group, $R^3$ is attached to the nitrogen carrying the $R^1$ substituent, otherwise to the nitrogen attached to the 16-position.

The quaternization is carried out in the presence of an aliphatic ketone or alcohol or methylene chloride. Preferably quaternization is performed in acetone, at room temperature.

The monoquaternary salts of the formula (Ib) are prepared from the diquaternary salts of the formula (Ia). The reaction is carried out in an alkanol having from 1 to 4 carbon atoms, preferably methanol or ethanol by adjusting the pH of the solution of the compound of formula (Ia) to 8.5 to 9, e.g. with sodium hydroxide. The reaction takes place also below pH 8.5 but considerably slower.

Once the solvent is eliminated, the alkali metal halide formed as a by-product is separated by phase exchange, and the compound of the formula (Ib) is purified, e.g. by crystallization.

The invention is elucidated in greater detail by the aid of the following non-limiting Examples.

EXAMPLE 1

3β-Hydroxy-17-bromo-androsta-5,16-diene 315 g (1.048 moles) of 3β-hydroxy-androst-5-ene-17-hydrazone are dissolved in 3150 ml of dry pyridine, the solution is cooled to 0° C., whereupon a solution of 280.3 g. (1.574 moles) of N-bromo-succinimide in 4000 ml of dry pyridine is added in 30 minutes. (The temperature must not exceed 10° C. during the addition.) Thereafter the reaction mixture is stirred for one hour, whereupon it is added to 30 lit. of ice water. After stirring for an additional hour, the precipitate is allowed to concentrate, filtered and washed pyridin-free with a 5% aqueous hydrochloric acid solution and subsequently neutral with water. The nutsch-wet precipitate is dissolved in 800 ml of benzene, water is separated from the insoluble solid (azine by-product). The benzene solution is dried over magnesium sulfate and purified on a chromatographic column containing 1500 g of silica gel. The desired product is eluted with benzene. Benzene is eliminated under reduced pressure, and the residue is dried until obtaining a steady weight.

Yield: 206.8 g (56%) of the title compound Melting point: 162° to 164° C. $^1$H-NMR spectrum (CDCl$_3$): δ0.86 s (3H), 107 s (3H), 2.06 s (1H) 3.45 br (1H), 5.32 m (1H), 5.8 m (1H)

EXAMPLE 2

17-Bromo-androsta-5,16-diene 100 g (0.35 mole) of androst-5-ene-17-hydrazone are dissolved in 860 ml of dry pyridine, the solution is cooled to 0° C. whereupon a solution of 75 g (0.41 mole) of N-bromo-succinimide in 1350 ml of dry pyridine is added in 30 minutes. (During the addition the temperature must not exceed 10° C.) Thereafter, the reaction mixture is stirred at 0° C. for two hours and is then added to 25 lit. of ice water. The precipitated substance is filtered off, washed with water, dissolved in 4000 ml of dichloromethane and washed with a 5% aqueous hydrochloric acid solution and subsequently with water. The organic layer is then dried over magnesium sulfate and the solvent is evaporated under reduced pressure. 91 g of a crude product are obtained, which is purified on a chromatographic column filled with 1200 g of silica gel. The elution is performed with benzene.

Yield: 47 g (40%) of the title compound. Melting point: 109° to 113° C. $^1$H-NMR spectrum (CDCl$_3$): δ0.87 s (3H), 1.05 s (3H), 5.25 s (1H), 5.8 s (1H).

The new androst-5-ene-17-hydrazone used as starting material is prepared as follows:

100 g (0.37 mole) of androst-5-ene-17-one are suspended in 1000 ml of ethanol. 170 ml (1.22 moles) of triethyl amine are added to the solution, followed by the dropwise addition of 500 ml (10.3 moles) of hydrazine hydrate. Thereafter, the reaction mixture is refluxed for two hours, cooled to room temperature and poured into 20 lit. of ice water. The precipitated white substance is filtered off, washed with water several times and dried.

Yield: 103 g (97%) of androst-5-ene-17-hydrazone Melting point: 140° to 142° C. $^1$H-NMR spectrum (CDCl$_3$): δ0.9 s (3H), 1.05 s (3H), 4.75 s (2H), 5.25 m (1H).

EXAMPLE 3

3β,17 -Diacetoxy-androst-5,16-diene 300 g (0.9 mole) of dehydroepiandrosterone acetate are dissolved in 1160 ml of isopropenyl acetate, whereupon a solution of 4 ml of concentrated sulfuric acid in 100 ml of isopropenyl acetate is added. The temperature of the reaction mixture is raised slowly (in two hours) to the boiling temperature of isopropenyl acetate, and continuously 400 ml of an acetone/isopropenyl acetate mixture are distilled off. After heating and continuous distillation for 6 hours, the solution is cooled to room temperature and added to 10000 ml of ice water, under stirring. The precipitous solution is allowed to stand at 5° to 10° C. for 12 hours, whereupon the precipitate is filtered off, washed acid-free with water, dried at room temperature and the crude product is crystallized from methanol.

Yield: 217 g (64%) of the title compound Melting point: 144° to 150° C.

EXAMPLE 4

3β-Hydroxy-5α,6α,16α,17α-diepoxy-17β-bromo-androstane 190 g (0.495 mole) of 3β-hydroxy-17β-bromo-androsta-5,16-diene are dissolved in 1900 ml of chloroform, whereupon 285 g (1.65 moles) of meta-chloro-perbenzoic acid are added within one hour, taking care that the temperature should remain between 10° to 20° C. Thereafter, the reaction mixture is stirred at room temperature for another 10 hours, diluted to twice its original volume with chloroform, washed acid-free with an aqueous sodium hydroxide solution cooled to 0° C. and dried over magnesium sulfate. The chloroform is distilled off and the residue is recrystallized from acetonitrile.

Yield: 126.4 g (61%) of the title compound Melting point: 150° to 153° C. $^1$H-NMR spectrum (CDCl$_3$): δ0.83 s (3H), 1.07 s (3H), 2.41 s (1H), 2.89 d (1H), 3.62 s (1H), 3.87 br (1H).

EXAMPLE 5

5α,6α,16α,17α-Diepoxy-17β-bromo-androstane

The title compound is prepared starting from 17β-bromo-androsta-5,16-diene, following the procedure described in Example 4, with a yield of 46.5%.

Melting point: 184° to 187° C. $^1$H-NMR spectrum (CDCl$_3$): δ0.82 s (3H), 1.06 s (3H), 2.85 d (J=3.5 Hz, 1H), 3.61 s (1H).

EXAMPLE 6

5α,6α,16α,17α-Diepoxy-3β,17β-diacetoxy-androstane 150 g (0.4 mole) of 3β,17β-Diacetoxy-androsta-5,16-diene are dissolved in 3100 ml (1.145 moles) of a perbenzoic acid solution containing 5.1% of ether, and the solution is allowed to stand at room temperature for 16 hours. When the reaction is complete, the precipitated crystalline product is filtered off and washed thoroughly with ether.

Yield: 65.0 g (39.9%) of the title compound. Melting point: 183° to 185° C.

The ethereal mother liquor is cooled to 0° C. and washed acid-free with a 10% aqueous sodium hydroxide solution cooled to 0° C. and subsequently neutral with water. The ethereal solution is dried over magnesium sulfate and is evaporated. The residue is recrystallized from acetone and then from acetonitrile, which affords another 36 g of the title compound.

Melting point: 183° to 185° C.

$^1$H-NMR spectrum (CDCl$_3$): δ0.85 s (3H), 1.10 s (3H), 2.0 s (3H), 2.08 s (3H), 2.88 d (1H), 3.82 s (1H), 4,9 m (1H).

EXAMPLE 7

3β-Hydroxy-5α,6α-epoxy-16β-(4'-methyl-1-piperazino)-androstane-17-one 26 g (0.067 mole) of 3β-hydroxy-5α,6α,16α,17α-diepoxy-17β-bromo-androstane are suspended in 260 ml of acetonitrile, whereupon 19 ml (0.17 mole) of freshly distilled N-methylpiperazine are added under vigorous stirring. The heterogenous system becomes homogenous within several minutes, whereupon the precipitation of the desired product starts rapidly. The precipitous solution is vigorously stirred for another 20 hours at room temperature, the precipitated crude product is filtered off, washed to almost neutral with water, and dried under reduced pressure until obtaining a steady weight. The product is then boiled in two 100 ml-portions of acetonitrile.

Yield: 19.4 g (79.8%) of the title compound Melting point: 233° to 235° C. $^1$H-NMR spectrum (CDCl$_3$): δ0.81 s (3H), 1.10 s (3H), 2.26 s (3H), 2.9 d (1H), 3.4 s (1H), 3.8 br, m (1H).

EXAMPLE 8

3β-Hydroxy-5α,6α-epoxy-16β-(1'-piperidino)-androstane-17-one

The title compound is prepared from 3β-hydroxy-5α,6α,16α,17α-diepoxy-17β-bromo-androstane, essentially following the procedure described in Example 7, with a yield of 83%.

Melting point: 152° to 155° C. $^1$H-NMR spectrum (CDCl$_3$): δ0.79 s (3H), 1.07 s (3H), 2.9 d (1H), 3.26 br (1H), 3.8 br (1H).

EXAMPLE 9

5α,6α-Epoxi-16β-(4'-methyl-1'-piperazino)-androstane-17-one

The title compound is prepared starting from 5α,6α,16α,17α-diepoxy-17β-bromo-androstane, essentially following the procedure described in Example 7, with a yield of 75%.

Melting point: 127° to 132° C. IR spectrum (KBr): 830, 1050, 1740, 2700, 2765, 2800 cm$^{-1}$

EXAMPLE 10

5α,6α-Epoxy-(1'-piperidino)-androstane-17-one

The title compound is prepared starting from 5α,6α,16α,17α-diepoxy-17β-bromo-androstane, essentially following the procedure described in Example 7, with a yield of 53%. Melting point: 135° to 138° C. IR spectrum (KBr): 860, 1040, 1735, 2800, 2830 cm$^{-1}$.

EXAMPLE 11

3β,5α-Dihydroxy-6β,16β-bis(4'-methyl-1'-piperazino)-androstane-17-one 60 g of 3β,17β-diacetoxy-5α,6α,16α,17α-diepoxy-androstane are dissolved in a mixture of 250 ml of freshly distilled N-methyl-piperazine and 37 ml of water, and the solution is refluxed for 110 hours, under nitrogen atmosphere. When the reaction is complete, which is monitored by thin layer chromatography, the excess of N-methyl-piperazine is distilled off under reduced pressure. The residue is dissolved in 1000 ml of dichloromethane and washed with three 200 ml portions of water. The solution is dried over magnesium sulfate, filtered off and the dichloromethane is removed.

The residue is triturated with a 1:1 mixture of acetone and ether, filtered and dried.

Yield: 49.6 g (66.8%) of the title compound Melting point: 239° to 242° C. $^1$H-NMR spectrum (CDCl$_3$+CD$_3$OD): δ0.86 s (3H), 1.10 s (3H), 2.27 s (6H), 4.0 br (1H).

EXAMPLE 12

3β,5α-Dihydroxy-6β,16β-bis(1'-piperidino)-androstane-17-one

The title compound is prepared starting from 3β,17β-diacetoxy-5α,6α,16α,17α-diepoxy-androstane, essentially following the procedure described in Example 11, with a yield of 58%.

Melting point: 202° to 205° C.

EXAMPLE 13

5α,6α-Epoxy-17β-hydroxy-16β-(4'-methyl-1'-piperazino)-androstane 18 g (0.046 mole) of 5α,6α-epoxy-17-oxo-16β-(4'-methyl-1'-piperazino)-androstane are dissolved in 450 ml of methanol. The solution is cooled to 0° C. and 3.6 g (0.095 mole) of sodium borohydride are added portionwise, under stirring and cooling. When the addition is complete, the reaction mixture is allowed to warm up to room temperature and stirred for another 24 hours. Thereafter the solvent is eliminated under reduced pressure, the residue is triturated with water and dried.

Yield: 16.65 g (92%) of the title compound Melting point: 161° to 165° C. $^1$H-NMR spectrum (CDCl$_3$): δ0.64 s (3H), 1.06 s (3H), 2.28 s (3H), 2.86 d (J=4 Hz, 1H), 3.39 d (J=9 Hz, 1H), 3.75 br (1H).

EXAMPLE 14

5α,6α-Epoxy-17β-hydroxy-16β-(1'-piperidino)-androstane

The title compound is prepared starting from 5α,6α-epoxy-17-oxo-16β-(1'-piperidino)-androstane, essentially following the procedure described in Example 13, with a yield of 89%.

Melting point: 140° to 144° C. IR spectrum (KBr): 2810, 2700, 1075, 1050, 880 cm$^{-1}$.

EXAMPLE 15

3β,17β-Dihydroxy-5α,6α-epoxy-16β-(1'-piperidino)-androstane

The title compound is prepared starting from 3β-hydroxy-5α,6α-epoxy-17-oxo-16β-(1'-piperidino)-androstane, essentially following the procedure described in Example 13, with a yield of 82%.

Melting point: 245° to 246° C. $^1$H-NMR spectrum (CDCl$_3$): δ0.63 s (3H), 1.07 s (3H), 2.9 d (1H), 3.38 d (1H), 3.83 m (1H).

EXAMPLE 16

3β,17β-Dihydroxy-5α,6α-epoxy-16β-(4'-methyl-1'-piperazino)-androstane

The title compound is prepared starting from 3β-hydroxy-5α,6α-epoxy-17-oxo-16β-(4'-methyl-1'-piperazino)-androstane, essentially following the procedure described in Example 13, with a yield of 96%.

Melting point: 174° to 176° C. $^1$H-NMR spectrum (CDCl$_3$): δ0.61 s (3H), 1.06 s (3H), 2.26 s (3H), 2.9 d (1H), 3.2 br (2H), 3.4 d (1H), 3.9 m (1H).

EXAMPLE 17

3β,5α,17β-Trihydroxy-6β-(1'-piperazino)-16β-(4'-methyl-1'-piperazino)-androstane 25 g (0.069 mole) of 3β,17β-dihydroxy-5α,6α-epoxy-16β-(4'-methyl-1'-piperazino)-androstane are dissolved in 250 ml of propyl alcohol, 80 g of piperazine and 24 ml of water are added, and the reaction mixture is refluxed under nitrogen atmosphere for 110 hours. When the reaction is complete, propyl alcohol, water and the excess of piperazine are eliminated under reduced pressure. The residue is triturated with water to eliminate piperazine traces, the precipitate is filtered, dissolved in chloroform, water is separated and the chloroform solution is dried. The solvent is distilled off under reduced pressure and the crude product is purified by mixing it with acetonitrile.

Yield: 22.3 g (66%) of the title compound Melting point: 210° to 215° C. $^1$H-NMR spectrum (CDCl$_3$): δ0.68 s (3H), 1.1 s (3H), 2.25 s (3H), 3.4 d (1H), 3.92 br (1H).

EXAMPLE 18

3β,5α,17β-Trihydroxy-6β-(1'-piperazino)-16β-(1'-piperidino)-androstane

The title compound is prepared starting from 3β,17β-dihydroxy-5α,6α-epoxy-16β-(1'-piperidino)-androstane, essentially following the procedure described in Example 17, with a yield of 86%.

Melting point: 180° to 185° C.

EXAMPLE 19

5β,17β-Dihydroxy-6β-(1'-piperazino)-16β-(4'-methyl-1'-piperazino)-androstane

The title compound is prepared starting from 5α,6α-epoxy-17β-hydroxy-16β-(4'-methyl-1'-piperazino)-androstane, essentially following the procedure described in Example 17, with a yield of 70%.

Melting point: 131° to 140° C. (decomp.) $^1$H-NMR spectrum (CDCl$_3$/DMSO/d$_6$): δ0.67 s (3H), 1.08 s (3H), 2.26 s (3H), 3.39 d (1H).

EXAMPLE 20

5α,17β-Dihydroxy-6β,16β-(4'-methyl-1'-piperazino)-androstane 9.8 g (0.025 moles) of 5α,6α-epoxy-17β-hydroxy-16β-(4'-methyl-1'-piperazino)-androstane are refluxed in a mixture of 175 ml (1.57 moles) of N-methyl-piperazine and 25 ml of water, under nitrogen atmosphere for 100 hours. The reaction mixture is evaporated under reduced pressure, the residue is triturated with water and dried. The product is purified by mixing it with acetonitrile.

Yield: 7.7 g (62%) of the title compound Melting point: 218° to 222° C. $^1$H-NMR spectrum (CDCl$_3$/DMSO/d$_6$): δ0.69 s (3H), 1.06 s (3H), 2.2 s and 2.23 s (2×3H), 3.41 d (J=9 Hz, 1H).

EXAMPLE 21

5α,17β-Dihydroxy-6β-(1'-piperidino)-16β-(4'-methyl-1'-piperazino)-androstane

The title compound is prepared starting from 5α,6α-epoxy-17β-hydroxy-16β-(4'-methyl-1'-piperazino)-androstane, essentially following the procedure described in Example 20, with a yield of 60%.

Melting point: 112° to 116° C. $^1$H-NMR spectrum (CDCl$_3$-CD$_3$OD): δ0.7 s (3H), 1.07 s (3H), 2.26 s (3H), 3.43 d (1H).

EXAMPLE 22

5α,17β-dihydroxy-6β-(4'-methyl-1'-piperazino)-16β-(1'-piperidino)-androstane

The title compound is prepared starting from 5α,6α-epoxy-17β-hydroxy-16β-(1'-piperidino)-androstane, essentially following the procedure described in Example 20, with a yield of 65%.

Melting point: 124° to 127° C. $^1$H-NMR spectrum (MeOD): δ0.71 s (3H), 1.11 s (3H), 2.25 s (3H), 3.4 d (1H).

EXAMPLE 23

3β,5α,17β-Trihydroxy-6β-(4'-methyl-1'-piperazino)-16β-(1'-piperidino)-androstane The title compound is prepared starting from 3β,17β-dihydroxy-5α,6α-epoxy-16β-(1'-piperidino)-androstane, essentially following the procedure described in Example 20, with a yield of 45%.

Melting point: 150° to 154° C. $^1$H-NMR spectrum (CDCl$_3$): δ0.66 s (3H), 1.08 s (3H), 2.21 s (3H), 3.27 d (J=8 Hz, 1H), 3.85 br (1H).

EXAMPLE 24

3β,5α,17β-Trihydroxy-6β-(1'-piperidino)-16β-(4'-methyl-1'-piperazino)-androstane The title compound is prepared starting from 3β,17β-dihydroxy-5α,6α-epoxy-16β-(4'-methyl-1'piperazino)-androstane, essentially following the procedure described in Example 20, with a yield of 49%.

Melting point: 154° to 157° C. $^1$H-NMR spectrum (CDCl$_3$): δ0.66 s (3H), 1.08 s (3H), 2.23 s (3H), 3.35 d (J=9 Hz, 1H), 3.8 br (1H).

EXAMPLE 25

3β,5α,17β-Trihydroxy-6β,16β-bis(1'-piperidino)-androstane 8.4 g (0.018 mole) of 3β,5α-dihydroxy-6β,16β-bis(1'-piperidino)-androstane-17-one are dissolved in a mixture of 70 ml of tetrahydrofurane and 42 ml of methyl alcohol. The solution is cooled to 10° C. and 6.7 g (0.18 mole) of sodium borohydride are added so that the temperature should remain between 10° C. and 20° C. The reaction mixture is stirred for another 4 hours, whereupon the solvent is eliminated under reduced pressure. The residue is dissolved in chloroform, washed with a 2% aqueous sodium hydroxide solution and subsequently with water, dried and the solvent is distilled off under reduced pressure. The crude product is purified by trituration with acetonitrile.

Yield: 4.4 g (52%) of the title compound Melting point: 146° to 150° C. $^1$H-NMR spectrum (CDCl$_3$): δ0.68 s (3H), 1.1 s (3H), 3.42 d (1H), 3.98 br (1H), 3.0–3.7 br (1H).

EXAMPLE 26

3β,5α,17β-Trihydroxy-6β,16β-bis(4'-methyl-1'-piperazino)-androstane

The title compound is prepared starting from 3β,5α-dihydroxy-6β,16β-bis(4'-methyl-1'-piperazino)-androstane-17-one, essentially following the procedure described in Example 25, with a yield of 72%.

Melting point: 235° to 237° C.

Alternatively, the title compound is prepared starting from 3β,17β-dihydroxy-5α,6α-epoxy-16β-(4'-methyl-1'-piperazino)-androstane, following the procedure described in Example 20.

Yield: 68% Melting point: 235° to 237° C.

EXAMPLE 27

3β,5α,17β-Trihydroxy-6β-[4'-(methoxycarbonylethyl)-1'-piperazino]-16β-(4'-methyl-1'-piperazino)-androstane 13 g (0.027 mole) of 3β,5α,17β-trihydroxy-6β-(1'-piperazino)-16β-(4'-methyl-1'-piperazino)-androstane are dissolved in 78 ml of chloroform, whereupon 15.6 ml (0.17 mole) of acrylic acid methyl ester are added to the solution. The reaction mixture is allowed to stand at room temperature for 24 hours, chloroform and the excess of acrylic acid methyl ester are distilled off, the residue is dissolved in ether and decolored on silica gel. The absorbent is filtered off, ether is eliminated by distillation and the residue is crystallized from acetonitrile.

Yield: 11 g (72%) of the title compound Melting point: 148° to 150° C. $^1$H-NMR spectrum (CDCl$_3$): δ0.65 s (3H), 1.06 s (3H), 2.23 s (3H), 3.2 br (1H), 3.33 d (1H).

EXAMPLE 28

3β,5α,17β-Trihydroxy-6β-[4'.(methoxycarbonylethyl)-1'-piperazino]-16β-(1'-piperidino)-androstane The title compound is prepared starting from 3β,5α,17β-trihydroxy-6β-(1'-piperazino)-16β-(1'-piperidino)-androstane, essentially following the procedure described in Example 27, with a yield of 80%.

Melting point: 100° C. $^1$H-NMR spectrum (CDCl$_3$): δ0.77 s (3H), 1.08 s (3H), 3.4 d (1H), 3.68 s (3H), 4.95 br (1H).

EXAMPLE 29

5α,17β-Dihydroxy-6β-[4'-(methoxycarbonylethyl)-1'-piperazino]-16β-(4'-methyl-1'-piperazino)-androstane The title compound is prepared starting from 5α,17β-dihydroxy-6β-(1'-piperazino)-16β-(4'-methyl-1'-piperazino)-androstane, essentially following the procedure described in Example 27, with a yield of 62%.

Melting point: 115° to 119° C. $^1$H-NMR spectrum (CDCl$_3$): δ0.66 s (3H), 1.05 s (3H), 2.26 s (3H), 3.39 d (1H), 3.68 s (3H).

EXAMPLE 30

3β,17β-Diacetoxy-5α-hydroxy-6β,16β-bis(4'-methyl-1'-piperazino)-androstane 10 g (0.019 mole) of 3β,5α,17β-trihydroxy-6β,16β-bis(4'-methyl-1'-piperazino)-androstane are dissolved in 100 ml of dichloromethane, and 8.6 ml (0.091 mole) of acetic anhydride and 4 ml (0.028 mole) of triethyl amine are added to the solution. The reaction mixture is allowed to stand at room temperature for 24 hours. The progress of the reaction is monitored by thin layer chromatography. When the reaction is complete, the excess of acetic anhydride is decomposed with 3 ml of water, the solution is diluted to twice its volume with dichloromethane and washed acid-free with a 10% aqueous sodium hydroxide solution cooled to 0° C. and subsequently neutral with water. The dichloromethane solution is dried over magnesium sulfate, the solvent is distilled off and the residue is crystallized from ether.

Yield: 6.9 g (59%) of the title compound Melting point: 140° C. $^1$H-NMR spectrum (CDCl$_3$): δ0.82 s (3H), 1.11 s (3H), 2.03 s (3H), 2.09 s (3H), 2.26 s (6H), 2.95 s (1H), 3–3.4 m (1H), 4.81 d (1H), 5.15 s, br (1H).

EXAMPLE 31

3β,17β-Diacetoxy-5α-hydroxy-6β-(1'-piperidino)-16β-(4'-methyl-1'-piperazino)-androstane The title compound is prepared starting from 3β,5α,17β-trihydroxy-6β-(1'-piperidino)-16β-(4'-methyl-1'-piperazino)-androstane, following the procedure described in Example 30, with a yield of 49%.

Melting point: 180° to 182° C. $^1$H-NMR spectrum (CDCl$_3$): δ0.80 s (3H), 1.09 s (3H), 2.03 s (3H), 2.08 s (3H), 2.28 s (3H), 2.8–3.3 m (1H), 4.69 d (J=9 Hz, 1H), 5 br (1H).

EXAMPLE 32

3β,17β-Diacetoxy-5α-hydroxy-6β,16β-bis(1'-piperidino)-androstane

The title compound is prepared starting from 3β,5α,17β-trihydroxy-6β,16β-bis(1'-piperidino)-androstane, essentially following the procedure described in Example 30, with a yield of 68%. Melting point: 125° to 129° C.

EXAMPLE 33

3β,17β-Diacetoxy-5α-hydroxy-6β-(4'-methyl-1'-piperazino)-16β-(1'-piperidino)-androstane The title compound is prepared starting from 3β,5α,17β-trihydroxy-6β-(4'-methyl-1'-piperazino)-16β-(1'-piperidino)-androstane, essentially following the procedure described in Example 30, with a yield of 72%.

Melting point: 145° to 147° C. $^1$H-NMR spectrum (CDCl$_3$): δ0.80 s (3H), 1.08 s (3H), 2.0 s (3H), 2.08 s (3H), 2.21 s (3H), 2.8–3.3 m (1H), 4.66 d (J=9.5 Hz, 1H), 5 br (1H).

EXAMPLE 34

5α-Hydroxy-6β,16β-bis(4'-methyl-1'-piperazino)-17β-acetoxy-androstane

The title compound is prepared starting from 5α,17β-dihydroxy-6β,16β-bis(4'-methyl-1'-piperazino)-androstane, essentially following the procedure described in Example 30, with a yield of 71%.

Melting point: 178° to 181° C. $^1$H-NMR spectrum (CDCl$_3$): δ0.82 s (3H), 1.03 s (3H), 2.08 s (3H), 2.25 s (6H), 4.74 d (J=9 Hz, 1H).

EXAMPLE 35

5α-Hydroxy-6β(1'-piperidino)-17β-acetoxy-16β-(4'-methyl-1'-piperazino)-androstane The title compound is prepared starting from 5α,17β-dihydroxy- 6β-(1'-piperidino)-16β-(4'-methyl-1'-piperazino)-androstane, essentially following the procedure described in Example 30, with a yield of 80%.

$^1$H-NMR spectrum (CDCl$_3$): δ0.83 s (3H), 1.09 s (3H), 2.10 s (3H), 2.27 s (3H), 4.8 d (J=9 Hz, 1H).

EXAMPLE 36

17β-Acetoxy-5α-hydroxy-6β-[4'-(methoxycarbonylethyl)-1'-piperazoino]-16β-(4'-methyl-1'-piperazino)-androstane The title compound is prepared starting from 5α,17β-dihydroxy-6β-[4'-(methoxycarbonlethyl)-1'-piperazino]-16β-(4'-methyl-1'-piperazino)-androstane, essentially following the procedures described in Example 30, with a yield of 98%. Melting point: 87° C. $^1$H-NMR spectrum (CDCl$_3$): δ0.80 s (3H), 1.06 s (3H), 2.08 s (3H), 2.23 s (3H), 3.68 s (3H), 4.75 d (J=10 Hz, 1H).

EXAMPLE 37

3β,17β-Diacetoxy-5α-hydroxy-6β-[4'-(methoxycarbonylethyl)-1'-piperazino]-16β-(1'-piperidino)-androstane The title compound is prepared starting from 3β,5α,17 β-trihydroxy-6β-[4'-(methoxycarbonylethyl)-1'-piperazino]-16β-(1'-piperidino)-androstane, essentially following the procedure described in Example 30, with a yield of 63%.

$^1$H-NMR spectrum (CDCl$_3$): δ0.79 s (3H), 1.09 s (3H), 2.03 s (3H), 2.08 s (3H), 3.68 s (3H), 4.76 d (1H), 5.1 br (1H).

EXAMPLE 38

3β,17β-Diacetoxy-5α-hydroxy-6β-[4'-(methoxycarbonylethyl)-1'-piperazino]-16β-(1'-piperazino)-androstane The title compound is prepared starting from 3β,5α,17β-trihydroxy-6β-[4'-(methoxycarbonylethyl)-1'-piperazino]-16β-(1'-piperidino)-androstane, essentially following the procedure described in Example 30, with a yield of 59%.

EXAMPLE 39

5α,17β-Dihydroxy-6β,16β-bis(4',4'-dimethyl-1'-piperazino)-androstane dibromide 1.2 g (2.24 mmoles) of 5α,17β-dihydroxy-6β,16β-bis-(4'-methyl-1'-piperazino)-androstane are dissolved in 80 ml of a 1:1 mixture of acetone and ethanol, and 20.6 ml (0.03 mole) of a 1.46 molar acetonic methyl bromide solution are added to the first solution. The flask is sealed and is allowed to stand in darkness. After two days the reaction mixture is partially evaporated under reduced pressure, the precipitated crystals are filtered off and purified by means of acetone.

Yield: 1 g (60%) of the title compound Melting point: 230° to 232° C. $^1$H-NMR spectrum (D$_2$O): δ0.86 s (3H), 1.07 s (3H), 3.36 s Example 40

40. példa

5α,17β-Dihydroxy-6β-(1'-piperidino)-16β-(4',4'-dimethyl-1'-piperazino)-androstane bromide The title compound is prepared starting from 5α,17β-dihydroxy-6β-(1'-piperidino)-16β-(4'-methyl-1'-piperazino)-androstane, in an acetone solution, following the procedure described in Example 39.

Yield: 70% Melting point: 248° to 252° C. $^1$H-NMR spectrum (CDCl$_3$/CD$_3$OD): δ0.78 s (3H), 1.09 s (3H), 3.21 s (6H).

EXAMPLE 41

5α,17β-Dihydroxy-6β-(4',4'-dimethyl-1'-piperazino)-16β-(1'-methyl-1'-piperidino)-androstane dibromide The title compound is prepared starting from 5α,17β-dihydroxy-6β-(4'methyl-1'-piperazino)-16β-(1'-piperidino)-androstane, in a 1:1 mixture of ethanol and chloroform, essentially following the procedure described in Example 39.

Yield: 72% Melting point: 240° to 251° C. $^1$H-NMR spectrum (MeOD): δ0.9 s (3H), 1.11 s (3H), 3.2 and 3.7 s (2×3H).

EXAMPLE 42

3β,5α,17β-Trihydroxy-6β-(4',4'-dimethyl-1'-piperazino)-16β-(1'-methyl-1'-piperidino)-androstane dibromide The title compound is prepared starting from 3β,5α,17β-trihydroxy-6β-(4'-methyl-1'-piperazino)-16β-(1'-piperidino)-androstane, in an acetone solution, essentially following the procedure described in Example 39.

Yield: 96% Melting point: 273° to 275° C. $^1$H-NMR spectrum (D$_2$O): δ0.83 s (3H), 1.08 s (3H), 3.1 s (9H), 4.0 br (2H).

EXAMPLE 43

3β,5α,17β-Trihydroxy-6β-(1'-piperidino)-16β-(1'-methyl-1'-piperidino)-androstane bromide The title compound is prepared starting from 3β,5α,17β-trihydroxy-6β,16β-bis(1'-piperidino)-androstane, in an acetone solution, essentially following the procedure described in Example 39.

Yield: 83% Melting point: 238° to 242° C. $^1$H-NMR spectrum (CDCl$_3$/CD$_3$OD): δ0.85 s (3H), 1.11 s (3H), 3.2 s (3H).

EXAMPLE 44

3β,5α,17β-Trihydroxy-6β-(1'-piperidino)-16β-(4',4'-dimethyl-1'-piperazino)-androstane bromide The title compound is prepared starting from 3β,5α,17β-trihydroxy-6β-(1'-piperidino)-16β-(4'-methyl-1'-piperazino)-androstane, in an acetone solution, essentially following the procedure described in Example 39.

Yield: 92% Melting point: 214° to 220° C. $^1$H-NMR spectrum (CDCl$_3$/CD$_3$OD 8-2): δ0.75 s (3H), 1.08 s (3H), 3.2 s (6H), 3.9 br (2H).

EXAMPLE 45

3β,5α,17β-Trihydroxy-6β,16β-bis(4',4'-dimethyl-1'-piperazino)-androstane diiodide The title compound is prepared starting from 3β,5α,17β-trihydroxy-6β,16β-bis(4'-methyl-1'-piperazino)-androstane, in a 3:1 mixture of acetone and methanol, essentially following the procedure described in Example 39.

Yield: 85% Melting point: 256° to 258° C.

EXAMPLE 46

3β,17β-Diacetoxy-5α-hydroxy-6β,16β-bis(4',4'-dimethyl-1'-piperazino)-androstane dibromide 5 g (0.008 mole) of 3β,17β-diacetoxy-5α-hydroxy-6β,16β-bis(4'-methyl-1'-piperazino)-androstane are dissolved in a mixture of 100 ml of dry acetone and 5 ml of dichloro-methane, and a solution of 3.22 g (0.033 mole) of methyl bromide in 18 ml of acetone is added to the first solution. The reaction mixture is allowed to stand at room temperature for 24 hours. The precipitation of the crystalline title compound starts within about 15 minutes. When the reaction is complete, the crystals are filtered off, washed thoroughly with acetone and dried until obtaining a steady weight.

Yield: 6.3 g (99%) of the title compound Melting point: 240° to 245° C. $^1$H-NMR spectrum (CDCl$_3$): δ0.83 s (3H), 1.07 s (3H), 2.03 s (3H), 2.12 s (3H), 3.42 br (12H), 4.79 d (1H).

EXAMPLE 47

3β,17β-Diacetoxy-5α-hydroxy-6β-(4',4'-dimethyl-1'-piperazino)-16β-(1'-methyl-1'-piperidino)-androstane dibromide The title compound is prepared starting from 3β,17β-diacetoxy-5α-hydroxy-6β-(4'-methyl-1'-piperazino)-16β-(1'-piperidino)-androstane, essentially following the procedure described in Example 46, with a yield of 75%.

Melting point: 268° to 270° C. (decomp.) $^1$H-NMR spectrum (CDCl$_3$/CD$_3$OD): δ0.90 s (3H), 1.08 s (3H), 2.01 s (3H), 2.16 s (3H), 3.23 br (9H), 4.3 br (1H), 5.15 br (1H), 5.25 d (1H).

EXAMPLE 48

5α-Hydroxy-6β,16β-bis(4',4'-dimethyl-1'-piperazino)-17β-acetoxy-androstane dibromide The title compound is prepared starting from 5α-hydroxy-6β,16β-bis(4'-methyl-1'-piperazino)-17β-acetoxy-androstane, essentially following the procedure described in Example 46, with a yield of 79%.

Melting point: 190° C. (decomp.) $^1$H-NMR spectrum (D$_2$O): δ0.77 s (3H), 1.06 s (3H), 2.11 s (3H), 3.16 s (12H), 4.8 d (1H).

EXAMPLE 49

5α-Hydroxy-6β-(1'-piperidino)-17β-acetoxy-16β-(4',4'-dimethyl-1'-piperazino)-androstane bromide The title compound is prepared starting from 5α-hydroxy-6β-(1'-piperidino)-17β-acetoxy-16β-(4'-methyl-1'-piperazino)-androstane, essentially following the procedure described in Example 46, with a yield of 80%.

Melting point: 198° to 203° C. $^1$H-NMR spectrum (CDCl$_3$): δ0.81 s (3H), 1.09 s (3H), 2.14 s (3H), 3.51 s (6H), 4.78 d (J=9 Hz, 1H).

EXAMPLE 50

3β,17β-Diacetoxy-5α-hydroxy-6β-(1'-piperidino)-16β-(4',4'-dimethyl-1'-piperazino)-androstane bromide The title compound is prepared starting from 3β,17β-di-acetoxy-5α-hydroxy-6β-(1'-piperidino)-16β-(4'-methyl-1'-piperazino)-androstane, essentially following the procedure described in Example 46, with a yield of 51.5%.

Melting point: 208° to 215° C. (decomp.) $^1$H-NMR spectrum (CDCl$_3$/CD$_3$OD): δ0.81 s (3H), 1.09 s (3H), 2.01 s (3H), 2.08 s (3H), 3.26 s (6H), 4.69 d (J=9 Hz, 1H), 5.0 br (J=20 Hz, 1H).

EXAMPLE 51

3β,17β-Diacetoxy-5α-hydroxy-6β-[4'-allyl-4'-(methoxycarbonylethyl)-1'-piperazino]-16β-(4'-allyl-4'-methyl-1'-piperazino)-androstane dibromide The title compound is prepared starting from 3β,17β-diacetoxy-5α-hydroxy-6β-[4'(methoxycarbonylethyl)-1'-piperazino]-16β-(4'-methyl-1'-piperazino)-androstane, essentially following the procedure described in Example 46, with a yield of 82%. $^1$H-NMR spectrum (CDCl$_3$/CD$_3$OD): δ0.81 s (3H), 1.06 s (3H), 2.01 s (3H), 2.08 s (3H), 3.15 s (3H).

EXAMPLE 52

3β,17β-Diacetoxy-5α-hydroxy-6β-[4'-methyl-4'-(methoxycarbonylethyl)-1'-piperazino]-16β-(4',4'-dimethyl-1'-piperazino)-androstane dibromide The title compound is prepared starting from 3β,17β-diacetoxy-5α-hydroxy-6β-[4'-(methoxycarbonylethyl)-1'-piperazino-16β-(4'-methyl-1'-piperazino)-androstane, essentially following the procedure described in Example 46, with a yield of 88%.

Melting point: 230° C. (decomp.) $^1$H-NMR spectrum (CDCl$_3$): δ0.80 s (3H), 1.15 s (3H), 2.04 s (3H), 2.11 s (3H), 3.07 s (3H), 3.18 s (6H), 3.73 s (3H).

EXAMPLE 53

3β,17β-Diacetoxy-5α-hydroxy-6β-[4'-(methoxycarbonylethyl)-4'-methyl-1'-piperazino]-16β-(1'-methyl-1'-piperidino)-androstane dibromide The title compound is prepared starting from 3β,17β-diacetoxy-5α-hydroxy-6β-[4'-methoxycarbonylethyl)-1'-piperazino]-16β-(1'-piperidino)-androstane, essentially following the procedure described in Example 46, with a yield of 93%.

Melting point: 235° to 240° C. (decomp.) $^1$H-NMR spectrum (CDCl$_3$): δ0.90 s (3H), 1.07 s (3H), 2.03 s (3H), 2.2 s (3H), 3.4 s (6H), 3.8 s (3H), 5.4 d (1H).

EXAMPLE 54

17β-Acetoxy-5α-hydroxy-6β-[4'-methyl-4'-(methoxycarbonylethyl)-1'-piperazino]-16β-(4',4'-dimethyl-1' piperazino)-androstane dibromide The title compound is prepared starting from 17β-acetoxy-5α-hydroxy-6β-[4'-(methoxycarbonylethyl)-1'-piperazino]-16β-(4'-methyl-1'-piperazino)-androstane, essentially following the procedure described in Example 46, with a yield of 85%.

Melting point: 230° to 240° C. (decomp.) $^1$H-NMR spectrum (D$_2$O): δ0.76 s (3H), 1.06 s (3H), 2.12 s (3H), 3.03 s (3H), 3.16 s (6H), 3.72 s (3H).

EXAMPLE 55

3β,17β-Diacetoxy-5α-hydroxy-6β-(1'-piperidino)-16β-(1'-methyl-1'-piperidino)-androstane bromide 0.5 g (0.89 mmole) of 3β,17β-diacetoxy-5α-hydroxy-6β,16β-bis(1'-piperidino)-androstane are dissolved in a mixture of 5 ml of acetone and 2 ml of dichloromethane, and a solution of 0.3 ml (5.5 mmole) of methyl bromide in 3 ml of acetone is added to the first solution. The flask is sealed and allowed to stand at room temperature for 18 hours. The reaction mixture is diluted with ether and the precipitated substance is filtered off.

Yield: 0.55 g (95%) of the title compound Melting point: 213° to 216° C. $^1$H-NMR spectrum (CDCl$_3$); δ0.8 s (3H), 1.07 s (3H), 2.0 s (3H), 2.12 s (3H), 2.16 s (3H), 2.73 br (1H), 3.33 s (3H), 5.4 d (1H).

EXAMPLE 56

3β,17β-Diacetoxy-5α-hydroxy-6β-(4'-methyl-4'-propyl-1'-piperazino)-16β-(1'-piperidino)-androstane bromide 1.0 g (0.0017 mole) of 3β-17β-diacetoxy-5α-hydroxy-6β-(4'-methyl-1'-piperazino)-16β-(1'-piperidino)-androstane are dissolved in 10 ml of acetone and 2 ml (0.022 mole) of propyl bromide are added to the solution. The reaction mixture is refluxed for 4 hours, cooled to room temperature and the product is precipitated with ether.

Yield: 207° to 210° C. $^1$H-NMR spectrum (CDCl$_3$/CD$_3$OD): δ0.8 s (3H), 1.06 s (3H), 2.03 s (3H), 2.1 s (3H), 3.2 s (3H), 4.8 d (1H), 5.0 (1H).

EXAMPLE 57

3β,17β-Diacetoxy-5α-hydroxy-6β-(4'-methyl-4'-propyl-1'-piperazino)-16β-(1'-methyl-1'-piperidino)-androstane dibromide 0.6 g (0.86 mmole) of 3β,17β-diacetoxy-5α-hydroxy-6β (4'-methyl-4'-propyl-1'-piperazino)-16β-(1'-piperidino)-androstane bromide are dissolved in 5 ml of acetone and 10 ml (5.2 mmoles) of acetonic methyl bromide are added to the solution. The flask is sealed and allowed to stand at room temperature for 24 hours. The reaction mixture is diluted with ether and the precipitated product is filtered off. The crude product is dissolved in ethyl alcohol, decolored with charcoal, precipitated with ether and filtered.

Yield: 0.6 g (88%) of the title compound Melting point: 245° to 250° C. (decomp.) $^1$H-NMR spectrum (D$_2$O): δ0.9 s (3H), 1.03 s (3H), 2.03 s (3H), 2.2 s (3H), 3.16 s (3H), 3.3 s (3H), 5.1 br (1H), 5.25 d (1H).

EXAMPLE 58

3β,17β-Diacetoxy-5α-hydroxy-6β-(4'-methyl-1'-piperazino)-16β-(4',4'-dimethyl-1'-piperazino)-androstane bromide 4 g (0.0048 mole) of 3β,17β-diacetoxy-5α-hydroxy-6β-[4'-(methoxycarbonylethyl)-4'-methyl-1'-piperazino]-16β-(4',4'-dimethyl-1'-piperazino)-androstane dibromide are dissolved in 20 ml of ethanol, the solution is cooled to 0° C. and the pH of the solution is adjusted to 8.5 to 8.9 with a 1N aqueous sodium hydroxide solution of 0° C., under control with potentiometric titration. Ethanol is then distilled off under reduced pressure, at an ambient temperature of 30° C. The residue is treated with dichloro methane, and the insoluble sodium bromide by-product is filtered off by means of charcoal. This treatment is repeated two more times. Dichloromethane is distilled off and the residue is crystallized from acetone.

Yield: 2.5 g (77%) of the title compound Melting point: 230° to 235° C. (decomp.) $^1$H-NMR spectrum (CDCl$_3$/CD$_3$OD): δ0.81 s (3H), 1.1 s (3H), 2.04 s (3H), 2.12 s (3H), 2.42 s (3H), 3.38 s (6H), 4.78 d (J=10 Hz, 1H), 5.1 br (1H).

EXAMPLE 59

3β,17β-Diacetoxy-5α-hydroxy-6β-(4'-allyl-1'-piperazino)-16β-(4'-methyl-4'-allyl-1-piperazino)-androstane bromide The title compound is prepared starting from 3β,17β-diacetoxy-5α-hydroxy-6β-[4'-allyl-4'-(methoxycarbonylethyl)-1'-piperazino]-16β-(4'-methyl-4'-allyl-1'-piperazino)-androstane dibromide, essentially following the procedure described in Example 58, with a yield of 95.5%.

Melting point: 180° to 185° C. $^1$H-NMR spectrum (CDCl$_3$/CD$_3$OD): δ0.8 s (3H), 1.1 s (3H), 2.03 s (3H), 2.11 s (3H), 3.23 s (3H), 4.25 m (4H).

EXAMPLE 60

3β,17β-Diacetoxy-5α-hydroxy-6β-(4'-methyl-1'-piperazino)-16β-(1'-methyl-1'-piperidino)-androstane bromide The title compound is prepared starting from 3β,17β-di-acetoxy-5α-hydroxy-6β-[4'-methyl-4'-(methoxycarbonylethyl)-1'-piperazino]-16β-(1'-methyl-1'-piperidino)-androstane dibromide, essentially following the procedure described in Example 58, with a yield of 74%.

Melting point: 220° to 230° C. $^1$H-NMR spectrum (CDCl$_3$/CD$_3$OD): δ0.83 s (3H), 1.1 s (3H), 2.0 s (3H), 2.18 s (3H), 2.3 s (3H), 3.32 s (3H), 4.6 br (1H), 5.05 br (1H), 5.26 d (1H).

EXAMPLE 61

5α-Hydroxy-17β-acetoxy-6β-(4'-methyl-1'-piperazino)-16β-(4',4'-dimethyl-1'-piperazino)-androstane bromide The title compound is prepared starting from 5α-hydroxy-17β-acetoxy-6β-[4'-methyl-4'-(methoxycarbonylethyl)-1'-piperazino]-16β-(4',4'-dimethyl-1'-piperazino)-androstane dibromide, essentially following the procedure described in Example 58, with a yield of 85%.

Melting point: 215° to 225° C. (decomp.) $^1$H-NMR spectrum (CDCl$_3$/CD$_3$OD): δ0.8 s (3H), 1.07 s (3H), 2.1 s (3H), 2.27 s (3H), 3.3 s (6H), 4.77 d (1H).

We claim:

1. A physiologically acceptable quaternary ammonium salt of the Formula (Ia), (Ib), (Ic) or (Id)

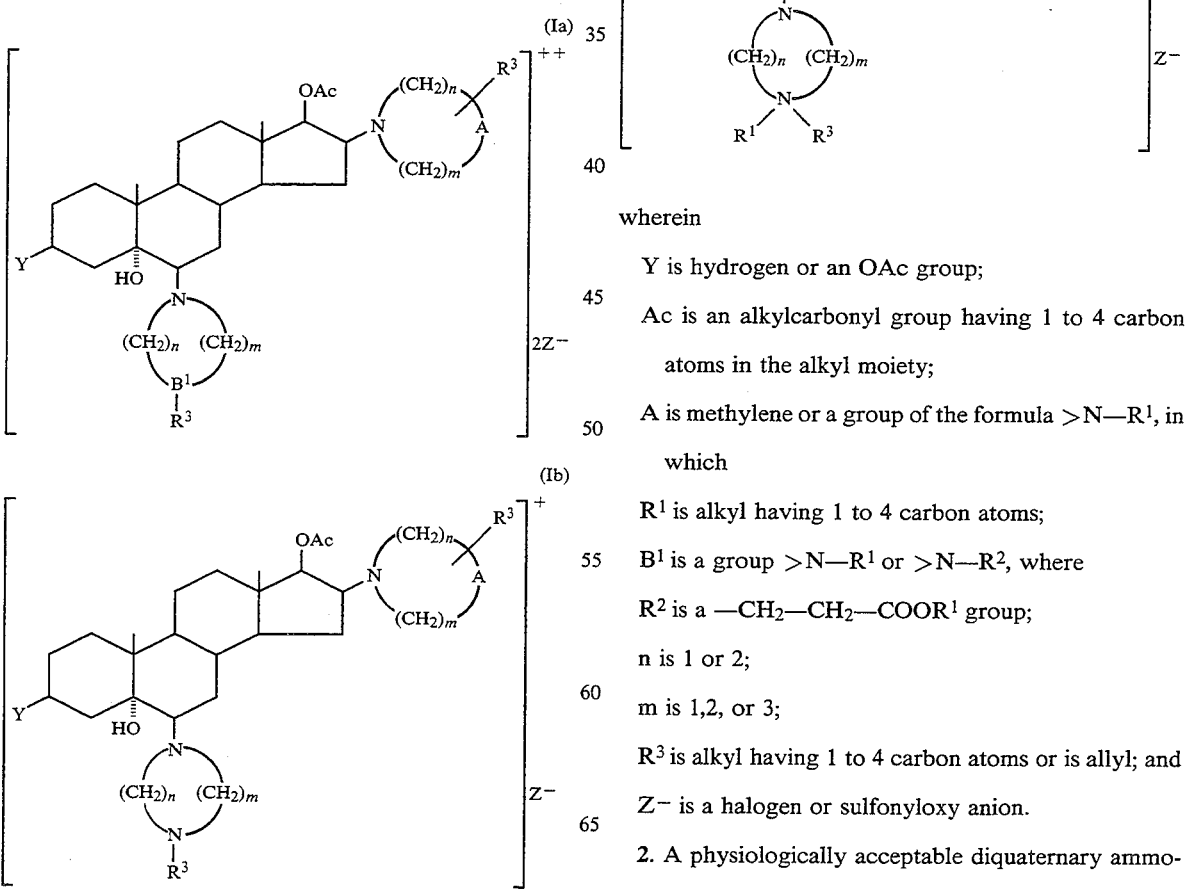

wherein

Y is hydrogen or an OAc group;

Ac is an alkylcarbonyl group having 1 to 4 carbon atoms in the alkyl moiety;

A is methylene or a group of the formula >N—R$^1$, in which

R$^1$ is alkyl having 1 to 4 carbon atoms;

B$^1$ is a group >N—R$^1$ or >N—R$^2$, where

R$^2$ is a —CH$_2$—CH$_2$—COOR$^1$ group;

n is 1 or 2;

m is 1, 2, or 3;

R$^3$ is alkyl having 1 to 4 carbon atoms or is allyl; and

Z$^-$ is a halogen or sulfonyloxy anion.

2. A physiologically acceptable diquaternary ammonium salt of the Formula (Ia)

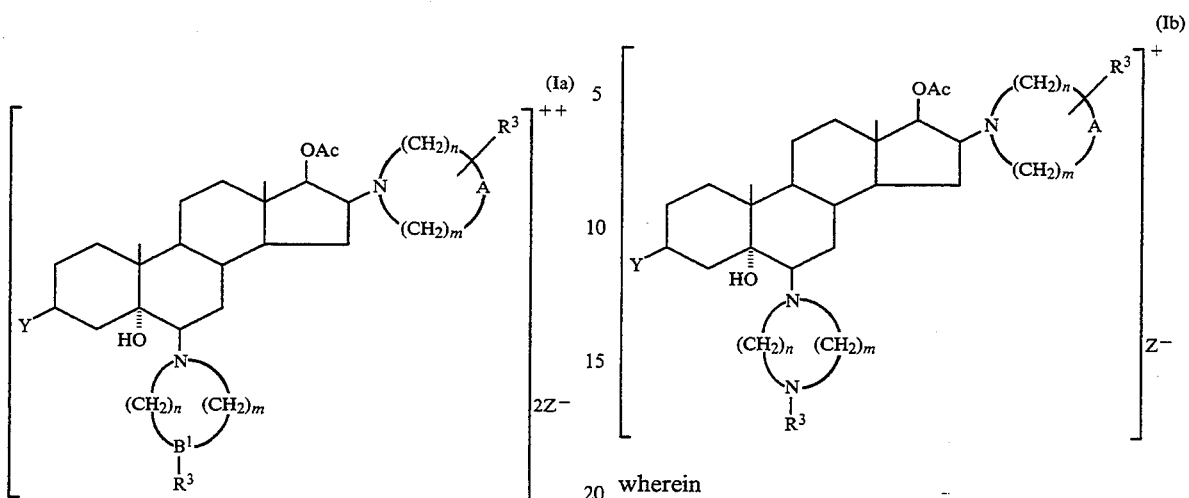

wherein

Y is hydrogen or an OAc group;

Ac is an alkylcarbonyl group having 1 to 4 carbon atoms in the alkyl moiety;

A is methylene or a group of the formula >N—R¹, in which

R¹ is alkyl having 1 to 4 carbon atoms;

B¹ is a group >N—R¹ or >N—R², where

R² is a —CH₂—CH₂—COOR¹ group;

n is 1 or 2;

m is 1, 2, or 3;

R³ is alkyl having 1 to 4 carbon atoms or is allyl; and

Z⁻ is a halogen or sulfonyloxy anion.

3. A physiologically acceptable monoquaternary salt of the Formula (Ib)

wherein

Y is hydrogen or an OAc group;

Ac is an alkylcarbonyl group having 1 to 4 carbon atoms in the alkyl moiety;

A is methylene or a group of the formula >N—R¹, in which

R¹ is alkyl having 1 to 4 carbon atoms;

n is 1 or 2;

m is 1, 2, or 3;

R³ is alkyl having 1 to 4 carbon atoms or is allyl; and

Z⁻ is a halogen or sulfonyloxy anion.

4. 3beta,17beta-diacetoxy-5alpha-hydroxy-6beta,1-6beta-bis(4',4'-dimethyl-1'-piperazino)-androstane dibromide as defined in claim 2.

5. 3beta,17beta-diacetoxy-5alpha-hydroxy-6beta(4',4'-dimethyl-1'-piperazino)-16beta-(1'-methyl-1'-piperidino)-androstane dibromide as defined in claim 2.

6. 5alpha-hydroxy-6beta,16beta-bis(4',4'-dimethyl-1'-piperazino)-17beta-acetoxy-androstane dibromide as defined in claim 2.

7. 3beta,17beta-diacetoxy-5alpha-hydroxy-6beta-{4'-(methoxycarbonylethyl)-4'-methyl-1'-piperazino}-16beta-(1'-methyl-1'-piperidino)-androstane dibromide as defined in claim 2.

8. 3beta,17beta-diacetoxy-5alpha-hydroxy-6beta-(4'-methyl-4'-propyl-1'-piperazino)-16beta-(1'-methyl-1'-piperidino)-androstane dibromide as defined in claim 2.

9. 3beta,17beta-diacetoxy-5alpha-hydroxy-6beta-(4'-methyl-1'-piperazino)-16beta-(4',4'-dimethyl-1'-piperazino)-androstane bromide as defined in claim 3.

10. 5alpha-hydroxy-17beta-acetoxy-6beta-(4'-methyl-1'-piperazino)-16beta-(4',4'-dimethyl-1'-piperazino)-androstane bromide as defined in claim 3.

* * * * *